(12) United States Patent
Horizumi et al.

(10) Patent No.: US 7,037,514 B1
(45) Date of Patent: May 2, 2006

(54) SHEET COSMETICS

(75) Inventors: Teruo Horizumi, Tokyo (JP); Hiromitsu Kawada, Tokyo (JP); Seiji Yamasaki, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/856,157

(22) PCT Filed: Dec. 3, 1999

(86) PCT No.: PCT/JP99/06800

§ 371 (c)(1),
(2), (4) Date: Jun. 1, 2001

(87) PCT Pub. No.: WO00/32154

PCT Pub. Date: Jun. 8, 2000

(30) Foreign Application Priority Data

Dec. 3, 1998 (JP) .................................. 10-344581

(51) Int. Cl.
*A01N 25/34* (2006.01)
*A61K 9/70* (2006.01)

(52) U.S. Cl. ..................................... 424/402; 424/443

(58) Field of Classification Search ................ 424/401, 424/78.03, 402, 443
See application file for complete search history.

(56) References Cited

U.S. PATENT DOCUMENTS

| | | |
|---|---|---|
| 5,026,552 A | 6/1991 | Gueret et al. |
| 5,456,745 A | 10/1995 | Roreger et al. |

FOREIGN PATENT DOCUMENTS

| | | | |
|---|---|---|---|
| JP | 60-243140 | | 12/1985 |
| JP | 60-244264 | | 12/1985 |
| JP | 60-246314 | | 12/1985 |
| JP | 03-81213 | | 4/1991 |
| JP | 8-188527 | | 7/1996 |
| JP | 8-188527 A | * | 7/1996 |
| JP | 10-502359 | | 3/1998 |
| JP | 10-309182 | | 11/1998 |
| JP | 11-269031 | * | 10/1999 |
| JP | 11-322535 | | 11/1999 |
| JP | 2003-510009 | | 3/2003 |
| JP | 2003-518008 | | 6/2003 |
| JP | 2003 518010 | | 6/2003 |

OTHER PUBLICATIONS

Patent Abstracts of Japan, JP 56-018917, Feb. 23, 1981.

* cited by examiner

*Primary Examiner*—Thurman K. Page
*Assistant Examiner*—Sharon Howard
(74) *Attorney, Agent, or Firm*—Oblon, Spivak, McClelland, Maier & Neustadt, P.C.

(57) ABSTRACT

Sheet cosmetics including a single-layered aqueous gel sheet having no supporting layer wherein the sheet of 1 mm in thickness has a light transmittance of 70% or more. These sheet cosmetics have high adhesion force to the skin, transparent appearance presenting no sense of incongruity and achieve excellent moistening and cooling effects on the skin.

14 Claims, 1 Drawing Sheet

SHEET COSMETICS

This Application is a 371 of PCT/JP99/06800 filed Dec. 3, 1999. This application claims priority to Japanese Application 10-344581 filed Dec. 3, 1998.

TECHNICAL FIELD

The present invention relates to a sheet cosmetic comprising an aqueous gel sheet in the absence of a supporting layer; exhibits highly adhesive to the skin; assumes transparent appearance; provides no sense of incongruity when applied to the skin; and achieves excellent moistening and cooling effects on the skin.

BACKGROUND ART

Conventionally, there have been known sheet cosmetics applied to the skin formed of a supporting sheet which is coated or impregnated with a gel composition containing, for example, a humectant or a whitening agent. The supporting sheet used above has an adequate level of strength and a shape-maintaining property as sheet cosmetics. Thus, the sheet cosmetics, is which the active ingredient is impregnated, are employed in order to attain effects such as permeating active ingredients to the skin and improving smoothness of the skin.

Generally, such a supporting sheet is formed of woven fabric or non-woven fabric. When the supporting sheet is coated or impregnated with a gel composition, the sheet becomes thicker. Therefore, such sheet cosmetics provide incongruent sensation during use. In addition, no such sheet of transparent appearance has been developed.

The gel composition applied or impregnated to the supporting sheet includes a natural polymer such as collagen, alginic acid or pullulan, or a synthetic polymer such as a cross-linked poly(acrylic acid) salt. Among these materials, a natural polymer material such as collagen or alginic acid, having high solubility in a cosmetic lotion or a similar product, exhibits insufficient shape-maintaining property as a cosmetic. In addition, because large amounts of sheet ingredients remain on the skin, such sheet cosmetics provide sticky sensation. To improve weakness of adhesion to the skin, an adhesive ingredient such as polyvinylpyrrolidone, poly(vinyl alcohol), or a poly(acrylic acid) salt is contained to the gel composition, or is formed into an adhesive surface layer (e.g., as disclosed in Japanese Kohyo Patent Publication No. 10-502359). However, such adhesive ingredients disadvantageously inhibit permeation of active ingredients and impart stickiness.

DISCLOSURE OF THE INVENTION

In view of the foregoing, the inventors have carried out extensive studies on mechanical and optical characteristics of material for producing sheet cosmetics, and have found a sheet cosmetic that exhibits strong adhesion to the skin; assumes transparent appearance; and provides unfavorable sensation when applied to the skin.

Accordingly, the present invention provides a sheet cosmetic comprising a single-layered aqueous gel sheet having no supporting layer, wherein the aqueous gel sheet of 1 mm in thickness has a light transmittance of 70% or more.

BEST MODES FOR CARRYING OUT THE INVENTION

Figure 1:
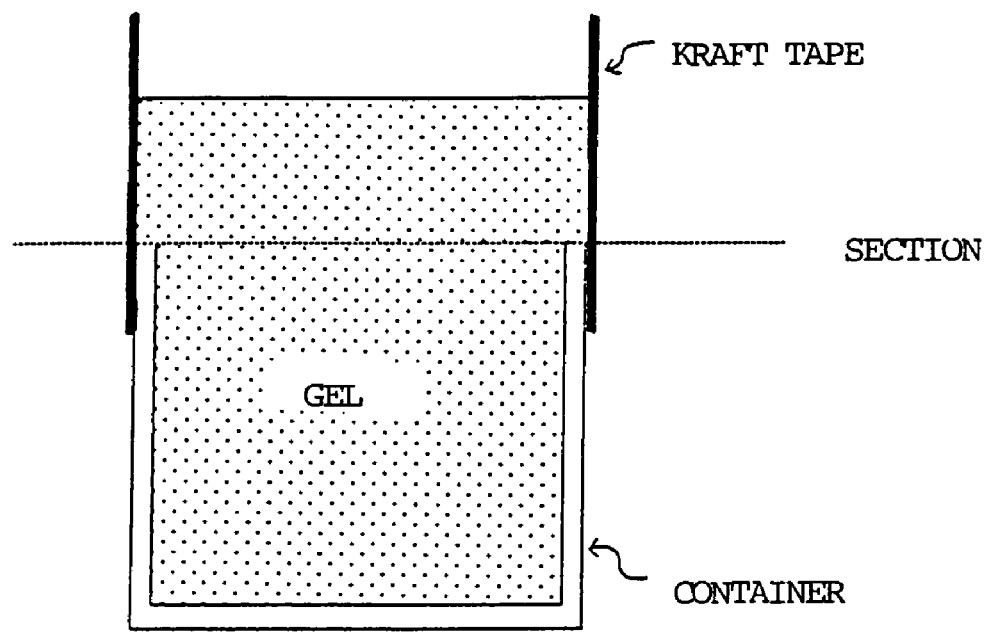
FIG. 1 shows a sample container for gel strength measurement of an agar sample and a cut surface.

The sheet cosmetic of the present invention comprises a single-layered aqueous gel sheet having no supporting layer. Conventional sheet cosmetics have a supporting layer formed of woven fabric or non-woven fabric, whereby the cosmetics are applied to the skin. In contrast, the sheet cosmetic of the present invention, having a single-layered aqueous gel which itself forms a sheet, has no such supporting layer.

In the sheet cosmetic of the present invention, the sheet of 1 mm in thickness has a light transmittance of 70% or more, preferably 80% or more, still preferably 85% or more. When the light transmittance is less than 70%, the sheet assumes no transparent appearance and provides considerable incongruent sensation when applied to the skin. The light transmittance at a wavelength of 550 nm can be measured, for example, by a UV spectrometer (UV-3100 PC, product of Shimadzu Corporation).

The sheet cosmetic of the present invention preferably has an adhesion force 1–100 times, more preferably 1–90 times, particularly preferably 1–50 times, its own weight. When the adhesion force is less than 1 time its own weight, the sheet cosmetic applied cannot be maintained on the skin and is readily released from the skin. When the adhesion force is in excess of 100 times, the sheet cosmetic provides a considerable incongruent sensation on the skin and an unfavorable irritation to the skin when removed. The adhesion force can be evaluated by affixing the sheet cosmetic to polyethylene-made circular parallel plates (having a diameter of 8 mm) at a force of 10 g for 10 seconds and, subsequently, measuring the force required to remove at a constant speed (1 mm/sec).

The sheet cosmetic of the present invention preferably exhibits the aforementioned adhesion in the form of a single-layered aqueous gel sheet without having an adhesive layer nor an adhesive ingredient. The term "adhesive layer" herein refers to a layer containing an adhesive ingredient such as polyvinylpyrrolidone, poly(vinyl alcohol), or a poly(acrylic acid) salt. Since conventional sheet cosmetics, which have themselves weak adhesion of gel component per se cannot be fixed on the skin, the adhesion to apply the sheet cosmetics to the skin is enhanced by use of the aforementioned adhesive ingredient. However, the sheet cosmetic of the present invention can be formed of a material providing the aforementioned adhesion, even though such adhesive layer or adhesive ingredient is contained.

The sheet cosmetic of the present invention preferably has a gel strength of 1000 $g/cm^2$ or less, particularly preferably 200–1000 $g/cm^2$, more preferably 200–800 $g/cm^2$, so as to mitigate incongruent sensation on the skin during use. The gel strength is measured in the following manner.

(1) Measuring Apparatus

Rheometer: RE-3305 (product of Sanden)

Plunger: Cylindrical plunger (diameter of 5 mm)

Sample-stage lowering speed: 0.5 mm/sec (2) Preparation of Samples

A sheet cosmetic sample is placed on a sample stage.

(3) Measurement of Gel Strength

A cylindrical plunger is lowered at a constant speed (0.5 mm/sec). The force received by the plunger is measured. A force at which the gel breaks is employed as the gel strength.

Gel-forming materials as described above may be selected from a variety of materials such as agar, mannan, and gelatin, so long as they exhibit the aforementioned property. For example, there can be used an agar ingredient (A), which is obtained by subjecting raw seaweed having a sulfate group content of 1–10% to extraction in neutral hot water and exhibits a gel strength of 600 g/cm$^2$ or less at an agar content of 1.5 wt. %.

The agar ingredient (A) is obtained by subjecting raw seaweed having a sulfate group content of 1–10% to extraction. Examples of such raw seaweed include *Gracilaria verracosa, Gelidium amansii*, and *Pterocladia capillacea*. Preferably, extraction is carried out in neutral hot water so as to obtain agar having a desirable physical property.

In view of sensation during use, the agar ingredient (A) of a 1.5 wt. % agar content preferably has a gel strength of 600 g/cm$^2$ or less, which is lower than that of typical agar, more preferably 10–600 g/cm$^2$, particularly preferably 10–400 g/cm$^2$. The gel strength is measured by use of apparatuses similar to the aforementioned apparatuses, in the following manner.

(1) Preparation of Samples

1) An agar sample (3.0 g) is measured precisely and placed in a container (volume 0.5 L) whose tare has been measured in advance, and ion-exchange water (50 mL) is added to the container so that the agar absorbs sufficient amounts of water.

2) Warm ion-exchange water is further added, to thereby adjust the content to approximately 210 g, and the resulting mixture is dissolved by heating for 15 minutes in a hot bath.

3) The content is adjusted to 200.0 g and the mixture is poured into a glass container (inner diameter of 49 mm, depth of 57 mm) with a tape around thereon as shown in FIG. 1.

4) The sample is cooled at room temperature for one hour, capped, and allowed to stand at 20° C. in a thermostat chamber for one night.

(2) Measurement of Gel Strength

After removing the tape, the portion of the gel protruding the upper edge of the container is cut by a cutter. The thus-formed surface of 1.5 wt. % aqueous gel is subjected to gel strength measurement by a rheometer.

The agar ingredient (A) of a 1.5 wt. % agar content preferably has a viscosity at 85° C. of ~15 mPa·s or more, particularly 15–200 mPa·s, in view of handling during production. In addition, the agar ingredient (A) preferably has an average molecular weight of 400,000–2,000,000. Furthermore, when a 1-mm-thick gel sample of the agar ingredient (A) of a 1.5 wt. % agar content is subjected to 20% deformation stress relaxation measurement, the time required for the initial stress to decrease to half the value is preferably 8 seconds (s) or longer, particularly preferably 8–15 seconds (s), in view of the shape-maintaining property. In other words, the shorter the stress relaxation time, the easier deformation occurs; i.e., the shape-maintaining property is poor. A stress relaxation time of 8 seconds or longer provides a favorable shape-maintaining property. The stress relaxation time is obtained by measuring a 20% compressively deformed sample by an apparatus (which is RSA2, product of Rheometrics) and circular parallel plates (having a diameter of 4.75 mm).

Gel-forming materials including the agar ingredient (A) are incorporated into the sheet cosmetic preferably in a total amount of 0.01–5 wt. %, particularly 0.1–3 wt. %, in view of strength and sensation during use. The balance is water and the following ingredients.

The sheet cosmetic of the present invention may further contain, as an additional ingredient, a water-soluble polymer (B) so as to improve strength and storage stability thereof. The water-soluble polymer to be used may be either natural or synthetic water-soluble polymer. Examples of the water-soluble polymer include polymers having a hydrophilic group such as a hydroxyl group, an ethylene oxide group, or an amido group, with polymers having a hydroxyl group being particularly preferred. Examples of such polymers include natural polymers such as polysaccharides and proteins, and synthetic polymers. Specific examples of the polysaccharides include cationized cellulose, carboxymethyl cellulose, hydroxyethyl cellulose, starch, ionized starch derivatives, block copolymers formed of starch and a synthetic polymer, hyaluronic acid, carrageenin, xanthan gum, chitin, chitosan, pullulan, tuberose polysaccharide, and alginic acid. Specific examples of the proteins include keratin, albumin, and collagen. Specific examples of the synthetic polymers include poly(vinyl alcohol)s and derivatives thereof, modified silicones, and latexes. Of these, polysaccharides are more preferred.

The water-soluble polymer (B) is incorporated into the sheet cosmetic preferably in an amount of 0.001–50 wt. %, particularly 0.01–10 wt. %.

The sheet cosmetic of the present invention may further contain a humectant (C). Examples of the humectant include ethanol, glycerin, ethylene glycol, propylene glycol, dipropylene glycol, 1,3-butylene glycol, 1,4-butylene glycol, polyglycerin such as diglycerin or triglycerin, glucose, maltose, maltitol, sucrose, fructose, threitol, erythritol, and starch sugar. Of these, ethanol, 1,3-butylene glycol, and glycerin are particularly preferred in view of sensation during use.

The sheet cosmetic contains the humectant (C) preferably in an amount of 0.001–40 wt. %, particularly preferably 0.01–30 wt. %.

Other than the aforementioned ingredients, the sheet cosmetic of the present invention may contain ingredients such as organic acids, oil, sterols, a surfactant, powder, silicones, inorganic salts, a preservative, a pH-regulator, a UV-absorber, a colorant, a pharmaceutically active ingredient, and a perfume.

The sheet cosmetic of the present invention is produced, for example, by dissolving a gel-forming material and other ingredients in warm water; pouring the resulting mixture into a mold; and cooling the mixture at a temperature not higher than the gelling temperature. Alternatively, the mixture is similarly molded into a sheet having a large area, followed by punching out sheet products of a desired shape.

The sheet cosmetic of the present invention preferably has a thickness of 0.1–5 mm, particularly preferably 0.5–2 mm, for attaining less incongruent sensation when applied to the skin.

No particular limitation is imposed on the shape of the sheet, and the sheet can be formed into an arbitrary shape. Specifically, in order to attain an enhanced adhesion to the skin, the sheet may be formed into a shape corresponding to the body part to which the sheet cosmetic is to be applied. Alternatively, when the sheet cosmetic is to be applied to the entirety of the face, the cosmetic sheet may be provided with holes corresponding to the eyes, the nose, and the mouth. Moreover, the sheet cosmetic may be formed into a cloud-like shape or a broad bean shape so as to enable the cosmetic to be applied to the under-eye area.

The sheet cosmetic of the present invention provides a cooling effect during application to the skin, through evaporation of water. Specifically, an aqueous gel for producing the sheet cosmetic of the invention is formed into a sheet of 1-mm thickness. By applying the sheet to the skin, maintaining for 10 minutes, and peeling off the sheet from the skin, the temperature of the skin surface can be lowered by 3° C. or more. The skin surface temperature is measured by means of a radiation surface thermometer (THI-500, product of TASCO).

The sheet cosmetic of the present invention can be used in a variety of modes. For example, the cosmetic is applied directly to the skin of the washed face or is applied to a portion of the skin where another cosmetic has already been applied. Alternatively, the sheet cosmetic of the present invention may first be coated with or impregnated with another cosmetic, then applied to the skin.

Due to the absence of a supporting layer, the sheet cosmetic of the present invention, after applied to the skin, shrinks on the skin as water evaporates, to thereby modify tension of the skin. Thus, the sheet cosmetic can effectively remove wrinkles and tone the skin. The shrinkage of the sheet is preferably 3% or more based on the total surface area, particularly preferably 3–20%, further preferably 3–10%, so that the skin conditions are corrected without unnatural sensation. The shrinkage of the sheet is obtained in the following manner: a sheet (2 cm×2 cm, thickness 1 mm) is applied to the skin (cheek) at room temperature; the changes in length (after 10 minutes) are measured by a slide caliper; and shrinkage is calculated.

lotion in an amount of 1.5%, and the resulting mixture was molded into a 1.2-mm-thick sheet. The gel strength (1.5 wt. % agar content) of samples a and b were 415 g/cm$^2$ and 610 g/cm$^2$, respectively. Similarly, a mannan sheet (c), non-woven fabric (d), and a pullulan sheet (e) were impregnated with the same commercial cosmetic lotion.

(Evaluation Methods)

(1) Skin Adhesion Sensation

For ten minutes following the application of a hydrogel to the face, skin adhesion sensation was evaluated by 10 specialized panelists on the basis of the following ratings:

○: at least 7 panelists answered "high skin adhesion sensation without incongruent sensation";

Δ: 4–6 panelists answered "high skin adhesion sensation without incongruent sensation"; and X: 3 or fewer panelists answered "high skin adhesion sensation without incongruent sensation."

(2) Adhesion Force

Adhesion force was measured by means of a tacking tester (TAC 2, product of RHESCA) under the aforementioned conditions.

(3) Gel Strength

As mentioned above.

(4) Stress Relaxation Time

As mentioned above.

(5) Light Transmittance

As mentioned above.

TABLE 1

|  | a | b | c | d | e |
|---|---|---|---|---|---|
| Sheet material | Agar 1 (invention) | Agar 2 | Mannan (invention) | Non-woven fabric | Pullulan |
| Sheet thickness (mm) | 1.2 | 1.2 | 1.2 | 1.5 | 1.5 |
| Light transmittance (%) | 95 | 88 | 96 | 40 | 90 |
| Adhesion force (times its own weight) | 4.2 | 3.6 | 5.6 | 0.9 | 1.1 |
| Skin adhesion sensation | ○ | Δ | ○ | X | X |
| Gel strength of sheet (g/cm$^2$) | 415 | 610 | 320 | — | — |
| Sol viscosity at 85° C. (mPa · s) | 12.5 | 13.8 | 10.8 | — | — |
| Mol. weight | 1,500,000 | 2,200,000 | 2,000,000 | — | — |
| Stress relaxation half time (s) | 8.5 | 5.3 | 8.0 | — | — |
| Sheet shrinkage (%) | 4.8 | 3.8 | 3.0 | — | — |

As disclosed in Japanese Patent Application Laid-Open (kokai) No. 9-143026, sheet cosmetics for removing wrinkles, which are fixed onto the skin while wrinkles are held extended, have conventionally been known. However, during use of such sheet cosmetics for removing wrinkles, the sheet cosmetics are difficult to apply to required parts in a suitable manner; e.g., the skin extended by the user's hands during application of the sheet cosmetics undesirably returns to a non-extended state. In addition, the sheet cosmetics provide incongruent sensation during use. In contrast, the sheet cosmetic of the present invention can easily modify tension of the skin.

EXAMPLES

Example 1

Sheet cosmetic samples shown in Table 1 were prepared and evaluated in terms of skin adhesive sensation. The results are shown in Table 1. In Table 1, samples "a" and "b" were prepared by dissolving agar in a commercial cosmetic As is clear from Table 1, the sheet cosmetics according to the present invention (sheets a and c) exhibit high light transmittance and provide excellent skin adhesive sensation. In contrast, the poly(acrylic acid) gel and gelatin gel have been found to exhibit shrinkage of 2.1% and 1.5%, respectively. Thus, the sheet cosmetics according to the present invention exhibit particularly excellent shrinkage.

Example 2

The water content and conditions of the skin to which the sheet cosmetic of the present invention had been applied were evaluated. Specifically, each of the sheet cosmetic of the present invention (the sheet a of Example 1) and a comparative sheet cosmetic (poly(acrylic acid) gel sheet cosmetic with a non-woven fabric support, thickness 2 mm) was applied and maintained in the skin for 15 minutes, and then peeled off from the skin. The above measurement was performed at 20° C. under dry conditions of a relative humidity of 15%. The water content was measured by Skicon-200 (product of IBS), and the obtained value was expressed as a relative value with respect to a beauty lotion serving as a standard. The skin texture, an index of the skin conditions, was observed as magnified under a microscope, and the texture was visually evaluated by specialists. The conditions of the skin texture before and after application of the sheet cosmetic were compared; the ratings of ○, Δ, and X were assigned for improvement of skin texture, slight improvement of skin texture, and no change, respectively. The results are shown in Table 2.

TABLE 2

|  | Agar 1 (invention) | Agar 2 | Poly(acrylic acid) + non-woven fabric |
|---|---|---|---|
| Skin water content (relative value) | 1.0 | 0.9 | 0.8 |
| Skin conditions (texture) | ○ | ○ | Δ |

As is clear from Table 2, the effect water content and skin conditions has been improved when the sheet cosmetic of the present invention is used.

Example 3

The efficacy of permeation of a water-soluble component (amino acid), during use of the sheet cosmetic of the present invention, was evaluated. Specifically, an amino acid was incorporated into each of the sheet cosmetic of the present invention and a comparative sheet cosmetic (each of sheet cosmetics of Example 2), and the thus-prepared sheet cosmetic sample was applied to pig skin. After eighteen hours, the amount of the amino acid permeating to the pig skin was measured. The amount is represented by a relative value on condition that the amount of amino acid taken in the pig skin by use of the sheet cosmetic of the present invention is 1. The results are shown in Table 3.

TABLE 3

|  | Agar 1 (invention) | Agar 2 | Poly(acrylic acid) + non-woven fabric |
|---|---|---|---|
| Amount of permeating amino acid (relative value) | 1.0 | 0.9 | 0.4 |

As is clear from Table 3, use of the sheet cosmetic of the present invention has been proven to improve the effect of promoting permeation of amino acid.

Example 4

The effect of cooling the skin provided by use of the sheet cosmetic of the present invention was evaluated.

Specifically, each of the sheet cosmetic of the present invention and a comparative sheet cosmetic (each of sheet cosmetics of Example 2) was applied to the face; maintained for 10 minutes; and then removed from the face. Subsequently, the skin temperature was monitored, to thereby evaluate the cooling effect. For comparison, the effect provided in the case in which only a lotion was applied to the face was also evaluated. The skin temperature was measured by means of a radiation thermometer (THI-500, product of TASCO). The results are shown in Table 4.

TABLE 4

| | Skin temperature (° C.) | | | |
|---|---|---|---|---|
| Time | Agar 1 (invention) | Agar 2 | Poly(acrylic acid) + non-woven fabric | Solo lotion |
| Before removal | 32.2 | 32.0 | 32.1 | 31.8 |
| Immediately after removal (0 min) | 28.1 | 28.8 | 30.3 | 30.9 |
| 3 min after | 29.1 | 29.6 | 30.9 | 31.5 |
| 5 min after | 29.6 | 30.8 | 31.3 | 31.8 |
| 10 min after | 30.8 | 31.2 | 32.3 | 32.1 |

As is clear from Table 4, use of the sheet cosmetic of the present invention has been proven to improve the cooling effect on the skin.

INDUSTRIAL APPLICABILITY

The sheet cosmetic of the present invention, which cosmetic forms an aqueous gel sheet even in the absence of a supporting layer, exhibits strong adhesion to the skin; assumes transparent appearance; and provides no sense of incongruity when applied to the skin. In addition, the sheet cosmetic is suitably applied to the skin; exhibits a high shape-maintaining property; and provides excellent temperature-maintaining and cooling effects on the skin. The sheet cosmetic can also modify tension of the skin through shrinkage by drying.

What is claimed is:

1. A sheet cosmetic comprising a single-layered aqueous gel sheet having no supporting layer, wherein an aqueous gel sheet of 1 mm in thickness has a light transmittance of 70% or more
    wherein said aqueous gel sheet comprises an agar (A) which has a gel strength of 600 g/cm$^2$ or less at an agar content of 1.5 wt %, wherein said agar ingredient (A) is obtained by subjecting raw seaweed having a sulfate group, content of 1–10% to extraction in neutral hot water.

2. A sheet cosmetic according to claim 1, having an adhesion force 1–100 time its own weight.

3. A sheet cosmetic according to claim 1, further comprising an additional water-soluble polymer (B).

4. A sheet cosmetic according to claim 1, further comprising a humectant (C).

5. The sheet cosmetic of claim 1, wherein said light transmittance is 80% or more.

6. The sheet cosmetic of claim 1, wherein said light transmittance is 85% or more.

7. The sheet cosmetic of claim 1, having an adhesion force 1–90 times its own weight.

8. The sheet cosmetic of claim 1, having an adhesion force 1–50 times its own weight.

9. The sheet cosmetic of claim 3, wherein said water-soluble polymer is present in an amount of 0.001 to 50 wt. %.

10. The sheet cosmetic of claim 3, wherein said water-soluble polymer is present in an amount of 0.01 to 10 wt. %.

11. The sheet cosmetic of claim 4, wherein said humectant is present in an amount of 0.001 to 40 wt. %.

12. The sheet cosmetic of claim 4, wherein said humectant is present in an amount of 0.01 to 30 wt. %.

13. The sheet cosmetic of claim 1, having a thickness of 0.1 to 5 mm.

14. The sheet cosmetic of claim 1, having a thickness of 0.5 to 2 mm.

* * * * *